United States Patent [19]

Gassman

[11] 4,080,341
[45] Mar. 21, 1978

[54] CARBAZOLENINE AND INDOLE COMPOUNDS

[75] Inventor: Paul G. Gassman, Columbus, Ohio

[73] Assignee: The Ohio State University Research Foundation, Columbus, Ohio

[21] Appl. No.: 712,538

[22] Filed: Aug. 9, 1976

Related U.S. Application Data

[62] Division of Ser. No. 573,069, Apr. 30, 1975, Pat. No. 3,992,392, which is a division of Ser. No. 355,198, Apr. 27, 1973, Pat. No. 3,901,899.

[51] Int. Cl.² ............................................ C07D 209/88
[52] U.S. Cl. ............................. 260/315; 260/326.27; 260/326.5 S; 260/326.62; 260/326.9
[58] Field of Search ............... 260/315, 326.9, 326.27, 260/326.5 S, 326.62

[56] References Cited

PUBLICATIONS

Gassman, "Chem. Abstracts" vol. 83, (1975), No. 193,079c.
Gassman et al., "J. Amer. Chem. Soc." vol. 95, (1972), pp. 590-592.
Gassman et al., "J. Amer. Chem. Soc." vol. 96, (1974), pp. 5495-5508.

*Primary Examiner*—Henry R. Jiles
*Assistant Examiner*—R. W. Ramsuer
*Attorney, Agent, or Firm*—Gordon W. Hueschen

[57] ABSTRACT

Preparing indoles and intermediates therefor by reacting an N-haloaniline with a β-carbonylic hydrocarbon sulfide to form an azasulfonium halide, reacting the azasulfonium halide with a strong base to form a thio-ether indole derivative, and then reducing the thio-ether indole, e.g. with Raney nickel, to form the indole compound. When an acetal or ketal of the β-carbonyl hydrocarbon sulfide is used, the azasulfonium salt is treated with a base, and then with an acid to form the thio-ether indole derivative. When an α-ethyl-β-carbonylic hydrocarbon sulfide is used, the resulting azosulfonium salt reacts with strong base to form a thio-ether indolenine derivative, which on reduction with Raney nickel or complex metal hydrides yields 3-substituted indoles. The aniline may be an aminopyridine to form an aza-indole compound in the process. The azasulfonium salts and thio-ether indole or thio-ether indolenine derivatives can be isolated and recovered from their respective reaction mixtures. The thio-ether-indole and thio-ether indolenine derivatives are useful as intermediates to make the indoles without the thio-ether group. The indoles are known compounds having a wide variety of uses, e.g., in making perfumes, dyes, amino acids, pharmaceuticals, agricultural chemicals and the like.

3 Claims, No Drawings

CARBAZOLENINE AND INDOLE COMPOUNDS

This application is a division of application Ser. No. 573,069, filed Apr. 30, 1975 now U.S. Pat. No. 3,992,392, which is in turn a division of application Ser. No. 355,198, filed Apr. 27, 1973, now issued U.S. Pat. No. 3,901,899, issued Aug. 26, 1975.

The invention described herein was made in the course of work under a grant or award from the Department of Health, Education and Welfare.

FIELD OF THE INVENTION

This invention relates to processes for making indoles. More particularly, this invention provides an improved process for preparing various substituted and unsubstituted indoles and intermediates therefor.

The Fischer indole synthesis [E. Fischer and F. Jourdan, Chem. Ber., 16, 2241 (1883); E. Fischer and O. Hess, ibid., 17, 559 (1884); E. Fischer, Justus Liebigs, An. Chem., 236, 126 (1886)., and B. Robinson, Chem. Rev., 69, 227 (1969)] has received the most widespread use because it, coupled with the Japp-Klingemann reaction [Chem. Ber., 20, 2942, 3284, 3398 (1887); Orq. Reactions, 10, 143, (1959)] has been the most versatile and widely applicable method of obtaining indoles up to this time. However, because of some inherent disadvantages to that process there is a need in the art for a more efficient, more economical process for making indole, indole intermediates, and indole derivatives.

Other prior art that might be considered pertinent is the following: a) P. Claus and W. Vycudilik, *Monatsh. Chem.*, 101, 396 (1970), wherein Claus et al reacted an aniline with a dimethylsulfoxide to form a sulfiliminic acid, not an azasulfonium salt; and b) P. Claus, W. Vycudilik, and W. Rieder, *Monatsh. Chem.*, 102, 1571 (1971), wherein these sulfiliminic compounds are thermally rearranged to hydrocarbon-S-hydrocarbon aromatic amine thio-ethers. Other papers which can be considered include our own publication in *Tetrahedron Letters*, No. 6, pp. 497–500 (1972) and that of Prof. C. R. Johnson et. al., *Tetrahedron Letters*, No. 6, pp. 501–504 (1972). In addition, the paper of U. Lerch and J. G. Moffatt entitled "Carbodiimide-Sulfoxide Reactions. XIII. Reactions of Amines and Hydrazine Derivatives" in the *Journal of Organic Chemistry*, Vol. 36, 3861 (1971) may be considered as pertinent as the Claus publications, supra. See also "The Chemistry of Indoles" by R. J. Sundberg, Academic Press, New York (1970) and "Indoles" Part I, by R. K. Brown, W. J. Houlihan Ed., Wiley Interscience, New York, (1972). Also, pertinent is our publication in J. Amer. Chem. Soc., 95, 590, 591 (1973).

SUMMARY OF THE INVENTION

Briefly, I have discovered that indoles can be prepared by reacting an N-haloaniline with a β-carbonyl hydrocarbon-S-hydrocarbon sulfide, or an acetal or ketal form thereof, under mild, substantially anhydrous conditions to form an azasulfonium halide salt, which can be isolated, if desired, and thereafter treating the azasulfonium salt with a base to form a thio-ether substituted indole or thio-ether substituted indolenine compound if a β-carbonyl sulfide or α-alkyl-β-carbonyl sulfide had been used, respectively, or with a base and then with acid if a β-carbonyl sulfide acetal or ketal had been used, to form the thio-ether substituted indole or thio-ether substituted indolenine. Thereafter, if desired, the thio-ether indole or thio-ether indolenine can be reduced, e.g., with Raney nickel, to remove the thio-ether group from the indole. This process is applicable to both anilines and aminopyridines. This process can be conducted through its several steps in one reaction vessel, without separation of the intermediate reaction products up to the isolation of the thio-ethers. However, in some cases it may be preferred for yield economies to isolate and at least partially purify the azasulfonium salt and thio-ether intermediates before continuing the process.

OBJECTS OF THE INVENTION

It is an object of this invention to provide an improved process for making indoles using primary and secondary aromatic amines and β-carbonyl sulfides or acetal or ketal forms of the β-carbonyl sulfides as reactants in the process.

It is another object of this invention to provide a process for making indoles and intermediates therefor which enables a less tedious synthesis and the use of more readily available, less expensive reactant chemicals under milder reaction conditions, which now permits the use of aniline starting materials containing substituents which otherwise could not be used.

Other objects, aspects and advantages of the invention will be apparent to the person skilled in this art from the specification and claims which follow.

DETAILED DESCRIPTION OF THE INVENTION

More specifically, this invention provides an improved process for making azasulfonium salt intermediates which are useful for making indoles which are known and which have a wide variety of known uses.

According to the process of this invention, a primary or secondary aniline or amino-pyridine starting material, both being referred to hereinafter as an aniline, is first reacted with a source of positive halogen to prepare the N-haloaniline. Many sources of positive halogen are known and can be used to form the N-haloanilines. Examples of positive halogen sources for this reaction include tertbutyl hypochlorite, N-chloro-succinimide, calcium hypochlorite, sodium hypochlorite, sodium hypobromite, and the like. The N-chloro anilines are preferred for reasons of availability of reactants to make them and cost of materials, but other positive halogen compounds can be used to make useful N-haloanilines for use in this process.

The essential features of the process comprise: (a) reacting under substantially anhydrous conditions in an organic diluent, at a temperature ranging from the Dry-Ice/acetone mixture temperatures (about −78° C) to about 20° C an N-halo-aniline of the formula

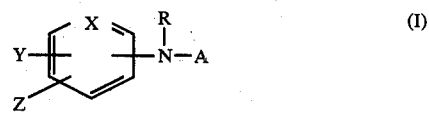

wherein R is hydrogen or a hydrocarbon radical free from aliphatic unsaturation containing from 1 to 8 carbon atoms:

A denotes chlorine or bromine, but is preferably chlorine:

X is —CH= or —N= and is in a position ortho, meta or para relative to the —N(R)A group;

each of Y and Z is hydrogen or is a substitutent which does not donate electrons more strongly than m-methoxy, m-hydroxy, or a p-acetoxy group, and not more than one of Y and Z, as a substituent, is ortho to the —N(R)A group position on the ring;

the —N(R)A group position on the ring having at least one ring carbon atom ortho thereto in an unsubstituted state;

with a β-carbonyl sulfide compound or a β-carbonyl sulfide acetal or ketal compound having a formula selected from the group consisting of

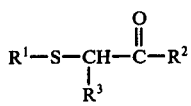   (II)

and

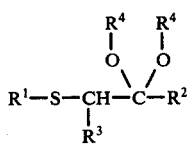   (III)

wherein R¹ is lower alkyl, or phenyl;

R² is hydrogen, lower alkyl, or phenyl;

R³ is hydrogen, lower alkyl, phenyl or benzyl;

R² can be attached to R³ as part of a cyclic ring system containing 5 to 8 carbon atoms, each R⁴ is lower alkyl or the two R⁴ radicals are taken together with the

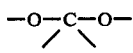

moiety to complete a cyclic ketal or acetal having from 3 to 4 carbon atoms in the ring, for a time sufficient to form an azasulfonium salt having a formula selected from the group consisting of

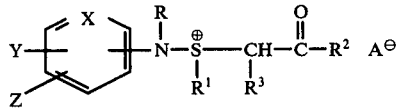   (IV)

and

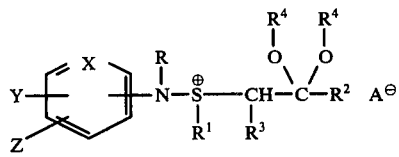   (V)

wherein X, Y, Z, R, R¹, R², R³, each R⁴ and A are as defined above;

(b) reacting the azasulfonium salt (IV) (R³ = H) with a substantially anhydrous base, that is, one whose conjugate acid has a pka greater than about 6, to effect rearrangement of the azasulfonium salt and to form a thio-ether compound of the formula

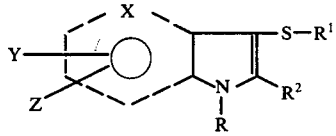   (VI)

wherein X, Y, Z, R, R¹, and R² are as defined above, and wherein the perforated hexagon containing X, Y and Z denotes a fused benzo (phenyl) or pyridyl ring in which X is in the 4-, 5-, 6- or 7- position relative to the indole ring nitrogen, when the azasulfonium salt had formula IV, that is, when the azasulfonium salt was derived from the free β-carbonyl sulfide reactant II (R³ = H); or reacting the azasulfonium salt of formula V (R³ = H) with substantially anhydrous base to form a compound of the formula VII

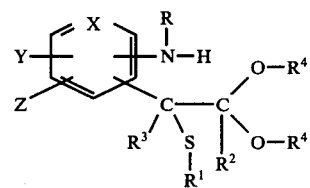   (VII)

wherein the —C(R³)(SR¹)[—C(OR⁴)₂R²] radical is ortho to the —N(R)H position on the ring;

(c) if compound VII is formed in step (b), treating the compound VII with acid, preferably an economical mineral acid such as aqueous hydrochloric acid, sulfuric acid, phosphoric acid, or the like, sufficient in amount and strength to effect hydrolysis of the OR⁴ ketal (or acetal) groups and to form a compound of the formula VI, above;

(d) reacting the azasulfonium salt (IV) (R³ = alkyl and R is hydrogen, or R³ and R² connected to form a ring and R is hydrogen) with a substantially anhydrous base, that is, one whose conjugate acid has a pKa greater than about 6, to effect rearrangement of the azasulfonium salt and to form a thio-ether compound of the formula

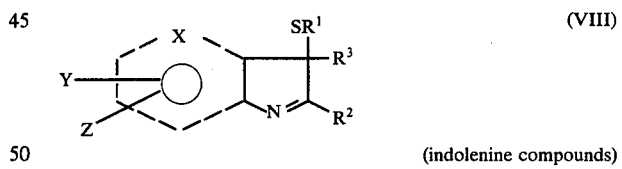   (VIII)

(indolenine compounds)

when X, Y, Z, R¹, R², and R³ are defined above, and wherein the perforated hexagon containing X, Y, and Z denotes a fused benzo (phenyl) or pyridyl ring in which X is in the 4-, 5-, 6-, or 7-position relative to the indole ring nitrogen, when the azasulfonium salt had formula IV, that is, when the azasulfonium salt was derived from the free β-carbonyl sulfide reactant II (R = H, R³ = alkyl, phenyl or benzyl or R³ connected to R² in a ring); or reacting the azasulfonium salt of formula V (R = H, R³ = alkyl, phenyl or benzyl or R³ connected to R² in a ring) with substantially anhydrous base to form a compound of the formula VII wherein the —C(R³)(SR¹)[-C(OR⁴)₂R₂] radical is ortho to the —NH₂ position on the ring;

(e) if compound VII (R = H and R³ = alkyl, phenyl or benzyl or R³ and R² connected to form a ring and R = H) is formed in step (b), treating the compound VII with acid, preferably an economical mineral acid such as aqueous hydrochloric acid, sulfuric acid, phosphoric acid, or the like, sufficient in amount and strength to effect hydrolysis of the $OR^4$ ketal (or acetal) groups and to form a compound of the formula VIII, above. (f) treating the indole derivative of formula VI from step (b) or from step (c), or the indolenine derivative of formula VIII from step (d) or from step (e) with a desulfurizing reducing agent, e.g., with Raney nickel or its equivalent, to form a compound having a formula selected from the group consisting of

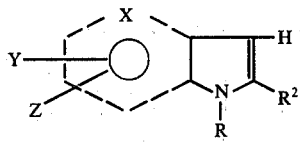

from the compound of formula VI, and

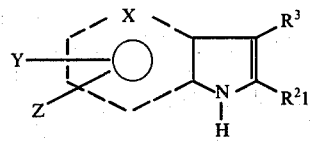

from the compound of formula VIII, wherein in each respective formula X, Y, Z, R, $R^2$ and $R^3$ are as defined above, and the perforated line hexagon has the same meaning as indicated above.

As used herein the term "lower alkyl" means a $C_1$ to $C_6$-alkyl radical, e.g., methyl, ethyl, propyl, isopropyl, n-butyl, isobutyl, tert-butyl, n-pentyl, neopentyl, n-hexyl, and the like. The term "lower alkyloxy" denotes a $C_1$ to $C_6$-alkyl—O— group wherein the $C_1$ to $C_6$-alkyl is as exemplified above. The term "lower acyloxy" denotes formyloxy and a $C_1$ to $C_6$-alkyl—C(O)O— group wherein the $C_1$ to $C_6$-alkyl is exemplified as above.

The aniline and aminopyridine compounds which can be used as starting materials in this process are those which have a free, unsubstituted carbon position on the aromatic ring ortho to the amino nitrogen group. Such compounds are known or are obtainable by known procedures. Many of them are described in publications such as "Chem Sources", Directories Publishing Co., Flemington, N.J. 08822 (1972). The aniline may be unsubstituted or may contain one or more substituents, preferably not more than two substituents on aromatic ring carbon atoms. The substituents should be atoms or groups which do not donate electrons more strongly than say, methoxy, in the meta-position or more strongly than acetoxy in the para or ortho positions. Not more than one of such substituents should be ortho to the —N(R)A group position. The —N(R)A group position of the aniline compound must have at least one ring carbon atom ortho thereto in the unsubstituted state. Examples of substituents which can be in the ring include halogen (fluorine, chlorine, bromine, iodine), nitro, cyano, N,N-di-loweralkylamino, lower alkyl, lower alkyloxy, lower acyloxy, (especially loweralkanoyloxy) a carbonyloxy-lower alkyl and carbonyloxy-phenyl groups. Examples of useful starting compounds include aniline, 3-chloroaniline, 4-chloroaniline, 3,4-dichloroaniline, 3-fluoroaniline, 4-fluoraniline, 3-bromoaniline, 4-bromoaniline, 4-iodoaniline, 3-nitroaniline, 4-nitroaniline, 3-cyanoaniline, 4-cyanoaniline, the toluidines such as 2-methylaniline, 3-methylaniline, 4-methylaniline, 4-ethylaniline, 4-hexylaniline, 3-propylaniline, 3-chloro-4-methylaniline, the lower alkyloxy-substituted anilines such as 3-methoxyaniline, 4-acetoxyaniline, 4-propionoxyaniline, 4-hexanoyloxyaniline, the 3- and 4-carbonyloxy-lower alkylanilines such as benzocaine (4-ethoxy-carbonylaniline), 4-methoxycarbonylaniline, 3-propoxycarbonylaniline, as well as 3-phenoxycarbonylaniline, 4-phenoxycarbonyl-aniline, and the aminopyridines such as 2-aminopyridine, 4-methyl-2-aminopyridine, 4-ethyl-2-aminopyridine, 4-hexyl-2-amino-pyridine, 4-methoxy-2-aminopyridine, 4-hexyloxy-2-aminopyridine, 3-aminopyridine, 4-amino-pyridine, 3-bromo-4-aminopyridine, 3-iodo-4-aminopyridine, 4-ethoxycarbonyl-2-aminopyridine, 4-chloro-2-aminopyridine, and the like. Secondary anilines and aminopyridines which may be used include those having a $C_1$ to $C_8$-hydrocarbon group bonded to the amino nitrogen and include the N-$C_1$ to $C_8$-alkylanilines and aminopyridines such as the N-methyl, N-ethyl, N-butyl, N-tert-butyl, N-octylanilines and aminopyridines as well as the N-phenyl, N-tolyl, N-xylylanilines and aminopyridines and the N-cycloalkylanilines and aminopyridines such as N-cyclopropyl, N-cyclobutyl, N-cyclopentyl, N-cyclohexyl and N-cyclooctylanilines and aminopyridines, and such compounds substituted on ring carbon atoms thereof with halogen, nitro, cyano, lower alkyl, lower alkyloxy, lower acyloxy, a carbonyloxy-lower alkyl or a carbonyloxy-phenyl as exemplified above.

The $\beta$-carbonyl sulfide and $\beta$-carbonyl sulfide acetal and ketal reactants of formulas II and III above, are exemplified by the acetonyl alkyl sulfides such as acetonyl methyl sulfide, acetonyl ethyl sulfide, acetonyl isopropyl sulfide, acetonyl butyl sulfide, acetonyl hexyl sulfide, and acetonyl phenyl sulfide, the alkylthioacetaldehydes such as the methylthioacetaldehyde, ethylthioacetaldehyde, isopropylthioacetaldehyde, butylthioacetaldehyde, pentylthioacetaldehyde, hexylthioacetaldehyde, phenylthioacetaldehyde, benzylthioacetaldehyde, as well as the alkylthio-, phenylthio- and benzylthio substituted ketones such as methylthiomethyl ethyl ketone, $\alpha$-ethylthioethyl ethyl ketone, $\alpha$-propylthio methyl hexyl ketone, $\alpha$-phenylthio butyl phenyl ketone, $\alpha$-ethylthio ethyl phenyl ketone, $\alpha$-methylthio-benzyl phenyl ketone, $\alpha$-ethylthioethyl benzyl ketone, methyl phenacetyl sulfide, 2-methylthiocyclohexanone, 2-methylthio cyclopentanone, 2-methylthiocycloheptanone, and the like, the dimethyl, diethyl, dipropyl dibutyl, dipentyl dehexyl and ethylene and propylene glycol acetal and ketal derivatives of such ketones and aldehydes. Use of the acetal or ketal form of the $\beta$-carbonyl sulfide reactant to form the azasulfonium salt results in the formation of an isolatable intermediate, having general formula VII, when the azasulfonium salt is treated with a base. Treatment of this ketal or acetal intermediate VII with an acid to hydrolyze the alkyl ketal or acetal protecting groups from the oxygen results in the formation of the indole thio-ether derivative of structure VI when $R^3=$ hydrogen, and the formation of the indolenine thio-ether derivative of structure VIII when R=H and $R^3=$alkyl or $R^3$ is connected to $R^2$ to form a ring. In some cases the yields of the indole thio-ether structure compound are higher by isolating the intermediate VII from its reaction mixture, and at least partially purifying it, before treating it with acid to form the indole thio-ether compound or the indolenine thio-ether derivative but it is not necessary to isolate intermediate VII in this process.

The reactions in this process up to the point of base addition are preferably conducted at relatively low temperatures, say, from the cooling temperatures obtained by using Dry Ice/acetone mixtures (about -78° C) to about 20° C, more preferably below about 0° C, although the reaction temperature becomes less critical after the azasulfonium salt is formed. When the base addition is completed the reaction mixtures need not be cooled. The reactions between the aniline and the halogenating agent to form the N-haloaniline, the N-haloaniline and the β-carbonyl sulfide reactant or the acetal or ketal form thereof to form the azasulfonium salt, and between the azasulfonium salt and the base are preferably done in an organic liquid solvent medium at a temperature below 0° C. Thereafter, the temperature of the mixture can be allowed to rise at room temperature. Acid, if necessary to treat the acetal or ketal groups, can be added at any convenient temperature, within the range indicated above, but preferably at say, 0° C to 50° C.

The reactions of this process can be conducted in a wide variety of inert organic solvents and diluents. Solvents as extreme in polarity as toluene and methanol can be used. Methylene chloride has been most commonly used, but solvents such as tetrahydrofuran, chloroform, acetonitrile and the like can also be used.

The azasulfonium halide salt and base treatment steps of the process are conducted under substantially anhydrous conditions; that is, a reasonable degree of care is taken to avoid the introduction of water into the reaction mixture during these steps, although the introduction of small incidental amounts of water introduced with solvents or reactants is not substantially detrimental to the process.

The base which is reacted with the azasulfonium salt, IV or V, can be any base which will cause formation of an ylid intermediate, which will undergo a Sommelet-Hauser type or rearrangement, and effect hydrogen transfer to produce the indole thio-ether VI or the acetal or ketal VII. Bases which can be used for this purpose are those which have a conjugate acid with a pKa of greater than about 6 and include, e.g., alkanolic alkali metal hydroxides such as methanolic sodium hydroxide, potassium hydroxide, lithium hydroxide and calcium hydroxide, as well as sodium methoxide, potassium methoxide, sodium and potassium ethoxides, potassium and sodium carbonates, and organic bases such as lower alkyl amines such as ethylamine, diethylamine, triethylamine, tributylamine, and aromatic amines such as pyridine, the lutidines, and the like.

Treatment of the azasulfonium salt with the base results in rapid conversion of the azasulfonium salt through its unisolated intermediates to the indole derivative having either formula VI or formula VIII if a β-carbonyl sulfide reactant had been used, or to the formation of intermediate having formula VII if the β-carbonyl sulfide acetal or ketal had been used. The intermediate produce VII can be isolated, if desired, but this is not necessary. The crude reaction mixture can be treated with acid to form indole derivative of formula VI or VIII depending on the nature of R and $R^3$.

As an example, a typical procedure could involve treating aniline in methylene chloride solution at -65° C with tert-butyl hypochlorite, to form the N-chloroaniline, followed by the addition of methyl thioacetaldehyde at -65° C, to form the azasulfonium salt and then with triethylamine to obtain 3-methylthio indole in 30 percent yield. Similar treatment of 4-chloroaniline gives 3-methylthio-6-chloroindole in 35 percent yield and 3-nitroaniline gives 3-methylthio-5-nitroindole in 38 percent yields. These thio-ether products can be isolated and treated with Raney nickel to reduce thioether indole derivatives; or with Raney nickel or an alkali metal aluminum hydride, or alkali metal borohydride, e.g., lithium aluminum hydride, sodium borohydride, or the like to reduce the methylthioindolenine compounds; or equivalent reducing agents by known procedures to remove the 3-thiomethyl groups and to form indole, 6-chlorindole, and 5-aminoindole, respectively. In the reductions, the nitro substituent is also reduced to the amino group, which can be advantageous for some uses of the indole product.

Preferred reactants for use in this process are those wherein a N-chloroaniline of an N-chloroaminopyridine is reacted with a lower α-alkylthio ketone or a lower α-alkylthio aldehyde, that is, those α-carbonyl sulfides wherein $R^1$ is lower alkyl, $R^2$ is hydrogen lower alkyl or phenyl, and $R^3$ is hydrogen or lower alkyl. When a ketal or an acetal of the α-carbonyl sulfide is used the preferred compounds are those wherein $R^1$ is lower alkyl, $R^2$ is hydrogen lower alkyl or phenyl, $R^3$ is hydrogen or lower alkyl and each $R^4$ is lower alkyl or cyclic. $R^2$ can be bonded to $R^3$ to form a ring, as indicated above.

Products produced by the process of this invention can be used for a wide variety of purposes. The 3-thio-ether indoles can be used as intermediates to make the indoles without the thio-ether group. Indole is known to be useful in perfumery in dilute concentrations. These compounds can be used as perfume bases, as intermediates for making plant hormones such as 3-indoleacetic acid, for making amino acids such as tryptophane, for making indigoid and thioindigoid type compounds which are useful as vat dyes for fabrics, pigments for paints, printing inks, plastics, etc. In addition, compounds produced by the process of this invention can be used as intermediates to prepare serotonin, antiserotonin, and some antipsychotic agents, antihypersive drugs and the like. See for example, A. Burger, *Medicinal Chemistry*, 3rd Edition, J. Wiley and Sons, New York, N.Y. (1970) pp. 70, 1038, 1413, 1451–1455, 1458–59, 1484–85; *J. Amer. Chem. Soc.*, 79, p. 3561 (1957); *Experientia*, 23, p. 298 (1967); *Experientia*, 16, 140 (1960); and M.S.L.D. Moustafa, *Japan Journal of Tuberc.*, 9, 65 (1961) for references to products which can be prepared by known procedures from the indoles and indole derivatives from this invention. Also, products of the process of this invention can be used to prepare the anti-inflammatory indomethacen and similar compounds disclosed in U.S. Pat. No. 3,161,654, as well as Indoxole, (an anti-inflammatory agent) indolmycin, an antibiotic, as well as compounds disclosed in U.S. Pat. No. 3,686,213 which are useful as diuretics, muscle relaxants, tranquilizers and inflammation inhibitors, for making antibacterial agents such as 5,6-dibromo-3-(2-aminoethyl) indolenine derivative in *Tetrahedron Letters*, (1973), page 299. The new compounds produced in the process of this invention are useful as intermediates in this process to prepare indoles and indole derivatives having the above exemplified uses.

The invention is further exemplified by the following detailed examples and preparations which are given by illustration only. Temperatures herein are in degrees centigrade unless otherwise indicated.

PREPARATION OF 3-METHYLTHIO-INDOLES

Methylthioacetaldehyde was obtained by refluxing 13 g. (0.095 mol) of methylthio-acetaldehyde dimethylacetal in 40 ml. of a 1 percent aqueous hydrochloric acid solution for 30 minutes. After cooling to room temperature, the solution was neutralized with saturated sodium bicarbonate solution and extracted with methylene chloride. The methylene chloride layer, after drying over anhydrous magnesium sulfate, filtering, and evaporating the solvent, gave a residue which was distilled to yield 5.24 g. (0.05 mol, 62 percent) of methylthioacetaldehyde, b.p. 129–134°; $n^{25}D$ 1.4810.

Two general procedures for the synthesis of indoles were used.

METHOD A. - SYNTHESIS OF INDOLES FROM ANILINES AND β-CARBONYL SULFIDES

To a vigorously stirred solution of about 0.044 mol of the aniline in 150 ml. of methylene chloride at −65°, was added dropwise a solution of 0.044 mol of tert-butyl hypochlorite in 20 ml. of the same solvent to form the N-chloroaniline. After 5 to 10 minutes, 0.044 mol of the β-carbonyl sulfide ($R^3$=H) dissolved in 20 ml. of methylene chloride was added causing an exotherm, and stirring at −65° C was continued for 1 hour to insure complete reaction to form the azasulfonium chloride salt. Usually the azasulfonium chloride salt had precipitated. Subsequently, 0.044 mol of triethylamine in 20 ml. of methylene chloride was added to the azasulfonium salt mixture. After the addition was completed, the cooling bath was removed and the solution was allowed to warm to room temperature. Both rearrangement and cyclization to form the 2-substituted indole were complete at this point. A 50 ml. portion of water was added and the organic layer was separated, dried, filtered and evaporated. The residue was further purified by column chromatography over silica gel using methylene chloride or a methylene chloride/chloroform mixture as the eluent.

Desulfurization of the 3-thio-ether indoles were accomplished by stirring a solution of 0.5 to 2.0 g. of the thio-ether indole in 50 ml. of absolute ethanol with an excess of W-2 Raney-nickel for 30 minutes. Filtration and evaporation gave a residue that was redissolved in methylene chloride and dried. After filtration, the solvent was removed leaving the pure de-sulfurized indole in yields varying from 70 to 82 percent.

W-2 Raney Nickel Preparation for Use

The W-2 Raney Nickel used in these experiments was obtained from W. R. Grace & Co., Raney Catalyst Division, South Pittsburg, Tenn., as No. 28 Raney Active Nickel Catalyst in Water. A portion of this was placed in a beaker and washed with distilled water until neutral to pH paper and then several more times with distilled water, three times with 95% ethanol, and three times with absolute ethanol. The catalyst under absolute ethanol was stored in brown bottles until use.

METHOD B. - SYNTHESIS OF INDOLES FROM ANILINES AND β-CARBONYL SULFIDE ACETALS AND KETALS

To a vigorously stirred solution of a 0.044 mol portion of the aniline in 150 ml. of methylene chloride at −65° there was added dropwise a solution of a 0.044 mol portion of tert-butylhypochlorite in 20 ml. of the same solvent to form the N-chloroaniline. After 5 to 10 minutes, a 0.044 mol portion of the β-carbonyl sulfide acetal or ketal ($R^3$=H) dissolved in 20 ml. of methylene chloride was added causing an exotherm, and stirring at −65° C was continued for about 1 hour to insure complete reaction to form the azasulfonium salt. Usually the azasulfonium salt had precipitated. Subsequently, a 0.044 mol portion of triethylamine in 20 ml. of methylene chloride was added. After the base addition was completed, the cooling bath was removed and the solution was allowed to warm to room temperature. A 50 ml. portion of water was added and the organic layer was separated, dried, filtered and evaporated, leaving an oily residue that mainly consisted of the unrearranged azasulfonium salt. To effect the rearrangement to intermediate compound VII the residue was refluxed in 150 ml. of carbon tetrachloride containing 5 ml. of triethylamine overnight or until rearrangement was complete. When all of the azasulfonium salt was rearranged the solvent was removed and the residue redissolved in 150 ml. of ethyl ether. Cyclization of the acetal or ketal intermediate to the indole ring system was effected by stirring this solution for 3 hours with 50 ml. of 2 N hydrochloric acid. After separation of the liquid layers, the ethereal layer was treated with saturated sodium bicarbonate solution, dried, filtered and evaporated. The residue containing the 3-thio-ether indole product was recovered. Further purification can be effected by column chromatography over silica gel using methylene chloride as the eluent.

Desulfurization of the 3-thio ether indole was accomplished in the manner indicated above to form the indole compound.

EXAMPLE 1 - PREPARATION OF INDOLE

A. α-Metylthio-α-(2-aminophenyl)-acetaldehyde dimethylacetate

The sub-titled compound was obtained from aniline and methylthioacetaldehyde dimethyl acetal following procedure B as far as the rearrangement. The product was purified by removal of the solvent to give an oily residue that was separated by column chromatography (silica gel-methylene chloride/ether 2:1) giving 5.70 g (0.025 mol, 57%) of the sub-titled compound. An analytical sample was obtained by distillation: bp 125°–128° (0.15 mm), $n^{25}D$ 1.5678; pmr (CCl$_4$) 2.82–3.67 (4H, aromatic protons), 5.39 (1H, d, J=7 Hz), 6.02 (1H, d, J=7 Hz), 6.17 (2H, broad s, NH$_2$), 6.65 and 6.88 (3H, s, diastereomeric OCH$_3$), and 8.22 (3H,s,SCH$_3$).

Anal. Calcd for $C_{11}H_{17}NO_2S$: C, 58.12; H, 7.54; N, 6.16; S, 14.11. Found: C, 58.01; H, 7.42; N, 6.15; S, 13.66.

B. Conversion of the dimethyl acetal from part A to 3-methylthioindole was accomplished by stirring 0.50 g (2.20 mmol) of the dimethylacetal dissolved in 25 ml of ethyl ether for 2 hr. with 10 ml of 0.5 N aqueous hydrogen chloride. The ethereal layer was separated, treated with a saturated sodium bicarbonate solution, dried, filtered and evaporated to yield 0.35 g (2.14 mmol, 97%) of the oily 3-methylthioindole. This 3-methylthioindole was treated with Raney nickel as described to form indole, identified by comparison with an authentic sample.

EXAMPLE 2 - PREPARATION OF 2-METHYLINDOLE

A. 2-Methyl-3-methylthioindole

This compound was obtained from N-chloroaniline and methylthioacetone following Method A, carried out on a 0.022 mol scale, which gave 2.68 g (0.015 mol, 69%) of the sub-titled product mp 58°–59° (recr. from cyclohexane), bp 140°–142° (0.85 mm); ir 3400 cm$^{-1}$(NH); pmr (CCl$_4$) 2.25–3.20 (5H, m, aromatic H), 7.76 and 7.83 (s, 3, CH$_3$ and SCH$_3$).

Anal. Calcd for C$_{10}$H$_{11}$NS: C, 67.75; H, 6.26; H, 7.90. Found: C, 67.61; H, 6.19; N, 7.87.

B. Desulfurization of the 2-methyl-3-methylthioindole (2.86 g, 0.022 mol) gave in 79% yield 2-methylindole, identified by comparison with an authentic sample.

EXAMPLE 3 - PREPARATION OF 2,5-DIMETHYLINDOLE

A. 2,5-Dimethyl-3-methylthioindole.

This compound was obtained from N-chloro-p-toluidine and methylthio-acetone following Method A which gave 5.05 g (0.0265 mol, 60%) of the sub-titled product: mp 110°–111° (recr. from cyclohexane); ir (KBr) 3350 cm$^{-1}$ (NH); pmr (CCl$_4$), 2.78 (1H, s, NH), 2.65 and 3.20 (1 resp. 2H, s, aromatic H), 7.58, 7.79 and 7.86 (3H, s, CH$_3$).

Anal. Calcd for C$_{11}$H$_{13}$NS: C, 69.09; H, 6.85; N, 7.33; S, 16.73. Found: C, 69.10; H, 6.86; N, 7.25; S, 16.73.

B. Desulfurization of 2,5-dimethyl-3-methylthioindole (0.50 g, 2.62 mmol) with Raney nickel gave in 80% yield 2,5-dimethylindole as indentified by comparison with an authentic sample.

EXAMPLE 4 - PREPARATION OF 5-ACETOXY-2-METHYLINDOLE

A. 5-Acetoxy-2-methyl-3-methylthioindole

This compound was obtained from N-chloro-4-acetoxyaniline and methylthioacetone following Method A, carried out on a 0.022 mol scale, which gave 3.55 g (0.015 mol, 68%) of the sub-titled product: mp 129°–129.5°, (recr. from methanol); ir (KBr) 3340 (NH) and 1710 cm$^{-1}$ (C=O); pmr (CCl$_4$), 1.90 (1H, s, NH) 2.92 and 3.48 (1 resp. 2H, s, aromatic H), 7.73, 7.78 and 7.94 (3H, s, CH$_3$).

Anal. Calcd for C$_{12}$H$_{13}$NO$_2$S: C, 61.25; H, 5.57; N, 5.95; S, 13.63. Found: C, 60.91; H, 5.61; N, 5.90; S, 13.57.

B. Desulfurization of the 5-acetoxy-2-methyl-3-methylthioindole (0.50g, 2.13 mmol) (with Raney nickel) gave in 72% yield 5-acetoxy-2-methyl-indole, mp 129°–132° (lit. 128°–130° ).

EXAMPLE 5 - PREPARATION OF 5-CHLORO-2-METHYLINDOLE

A. 5-Chloro-2-methyl-3-methylthioindole

This compound was prepared from N-chloro-4-chloroaniline and methylthioacetone following Method A, which gave 6.68 g (0.032 mol, 72%) of the sub-titled product: mp. 64°–64.5° (recr. from cyclohexane ir (KBr) 3350 cm$^{-1}$ (NH); pmr (CCl$_4$), 2.42 (1H, s, NH), 2.52 and 3.15 (1 resp. 2H, m, aromatic H), 7.72 and 7.90 (3H, s, CH$_3$ and SCH$_3$).

Anal. Calcd for C$_{10}$H$_{10}$ClNS: C, 56.73; H, 4.76; N, 6.62; S, 15.14 Found: C, 56.73; H, 4.72; N, 6.56; S, 15.25.

B. Desulfurization of 5-chloro-2-methyl-3-methylthioindole (1.0 g, 4.73 mmol) gave in 74% yield 5-chloro-2-methylindole (mp 99°–100.5°, lit. 117°–119° ) as confirmed by comparison of its ir spectrum with that of an authentic sample.

EXAMPLE 6 - PREPARATION OF 4-NITRO-2-METHYL-3-METHYLTHIOINDOLE

A. 2-Methyl-3-methylthio-4-nitroindole

This compound was obtained from N-chloro-3-nitroaniline and methylthioacetone following Method A with the modifications that (a) tetrahydrofuran (THF) was used as the solvent in view of the solubility of (b) the mixture was stirred for 1 hr. after addition of the hypochlorite and 2 hr. after addition of the sulfide. In this way 8.07 g (0.036 mol, 82%) of 4-nitro-2-methyl-3-methylthioindole was isolated: mp 148°–150° recr. from a CCl$_4$/CHCl$_3$ mixture); ir (KBr) 3300 cm$^{-1}$(NH); pmr (CDCl$_3$), 1.10 (1H, s, NH), 1.75–3.00 (3H, m, aromatic H), 7.40 and 7.75 (3H, s, CH$_3$ and SCH$_3$).

Anal. Calcd for C$_{10}$H$_{10}$N$_2$O$_2$S: C, 54.04; H, 4.54; N, 12.60; S, 14.42. Found: C, 54.09; H, 4.58; N, 12.62; S, 14.49.

EXAMPLE 7 - PREPARATION OF 2.7-DIMETHYLINDOLE

A. 2,7-Dimethyl-3-methylthioindole

This compound was obtained from N-chloro-2-methylaniline and methylthioacetone following Method A, which gave 6.04 g (0.0316 mol, 72%) of the sub-titled product: mp 59.5°–60.5° (recr. from cyclohexane); ir (KBr) 3360 cm$^{-1}$ (NH); pmr (CCl$_4$), 2.30–3.60 (4H, m, aromatic H), 7.66, 7.74 and 7.85 (3H, s, CH$_3$, NCH$_3$, and SCH$_3$).

Anal. Calcd for C$_{11}$H$_{13}$NS: C,69.06; H, 6.85; N, 7.32 Found: C,69.05; H, 6.85; N, 7.24.

B. Desulfurization of 2,7-dimethyl-3-methylthioindole (1.0 g, 5.23 mmol) gave in 73% 2,7-dimethylindole, mp 32°–33° (lit. 33°–35° ).

EXAMPLE 8 - PREPARATION OF 1,2-DIMETHYLINDOLE

A. 1,2-Dimethyl-3-methylthioindole

This compound was obtained from N-chloro-N-methylaniline and methylthioacetone following Method A. In this case, the organic layer was extracted twice with 2N aqueous hydrochloric acid, after it has been hydrolyzed with 50 ml of water. From the acid extracts 1.53 g (32.5%) of N-methylaniline could be recovered. The organic layer gave in the usual work-up procedure 3.02 g (0.016 mol, 36%, or 54% based on unrecovered starting aniline) of the sub-titled product: mp 59.5°–60° (recr. from n-hexane); pmr (CCl$_4$), 2.45 and 2.96 (1 and 3H, m, aromatic H), 6.62 (3H, s, NCH$_3$), 7.65 and 7.87 (3H, s, CH$_3$ and SCH$_3$).

Anal. Calcd for C$_{11}$H$_{13}$NS: C, 69.06; H, 6.85; N, 7.32. Found: C,68.77; H,6.79; N,7.26.

B. Desulfurization of 1,2-dimethyl-3-methylthioindole (1.0 g, 5.23 mmol) gave in 76% yield 1,2-dimethylindole, mp 50°–52° (lit. 56°).

EXAMPLE 9 - PREPARATION OF 2-PHENYLINDOLE

A. 3-Methylthio-2-phenylindole

This compound was obtained from N-chloroaniline and methyl phenacylsulfide following Method A, which gave 8.57 g (0.036 mol, 81%) of the sub-titled product: mp 106°–107° (recr. from 95% ethanol); ir (KBr) 3300 cm$^{-1}$ (NH); pmr (CCl$_4$), 2.00–3.00 (10H, m, aromatic H) and 7.84 (3H, s, SCH$_3$).

Anal. Calcd for C$_{15}$H$_{13}$NS: C,75.28; H,5.48; N,5.85. Found: C,75.16; H,5.50; N,5.85.

B. Desulfurization of 3-methylthio-2-phenylindole (1.55 g, 6.50 mmol) gave in 74% yield 2-phenylindole, mp 186.5°–187.5° (lit. 186°), which ir spectrum was identical to that of an authentic sample.

EXAMPLE 10 - PREPARATION OF INDOLE

A. 3-Methylthioindole

This compound was obtained from N-chloroaniline and methylthioacetaldehyde following Method A which gave 1.06 g (6.5 mmol), 30%) of the sub-titled product: bp 112.5°–113° (0.15 mm), n$^{25}$D 1.6488; ir 3340 cm$^{-1}$ (NH); pmr (CCl$_4$), 2.40 and 3.05 (2 resp. 4H, m, aromatic H) and 7.82 (3H, s, SCH$_3$).

Anal. Calcd for C$_9$H$_9$NS: C,66.22; H,5.56; N,8.58. Found: C,66.11; H,5.57; N,8.52.

B. Desulfurization of 3-methylthioindole (1.7 g, 0.01 mol) gave indole in 82% yield, as confirmed by comparison with an authentic sample.

EXAMPLE 11 - PREPARATION OF 5-CHLOROINDOLE

A. 5-Chloro-3-methylthioindole

This compound was obtained from N,4-dichloroaniline and methylthioacetaldehyde following Method A, but using tetrahydrofuran as the solvent. On column chromatography 1.72 g of the starting aniline could be recovered and 3.00 g (0.0152 mol, 35%, or 50% calculated on unrecovered aniline) of the sub-titled product was isolated; bp 134.5°–135.5° (0.20 mm); ir 3370 cm$^{-1}$ (NH); pmr (CCl$_4$), 1.90 (1H, s, NH), 2.37 (1H, s, aromatic H), 2.93 (3H, m, aromatic H) and 7.72 (3H, s, SCH$_3$).

Anal. Calcd for C$_9$H$_8$ClNS: C,54.68; H,4.08; N,7.09; S,16.22.

Found: C,54.44; H,4.13; N,7.13; S,16.02.

B. Desulfurization of 5-chloro-3-methylthioindole with Raney nickel gives 5-chloroindole.

EXAMPLE 12 - PREPARATION OF 3-METHYLTHIO-4-NITROINDOLE

A. 3-Methylthio-4-nitroindole

This compound was obtained from N-chloro-3-nitroaniline and methylthioacetaldehyde following Method A, with the modification that tetrahydrofuran was used as the solvent. In addition, the mixture was stirred for 1 hr after addition of the hypochlorite. After hydrolysis with water, the reaction mixture was extracted with 1N aqueous hydrochloric acid to remove any remaining nitroaniline. In this way 3.50 g (0.017 mol, 38%) of 3-methylthio-4-nitroindole was obtained as a black crystalline material; mp 123°–124° (recr. from ethanol); ir (KBr) 3310 cm$^{-1}$ (NH); pmr (CDCl$_3$), 1.03 (1H, s, NH), 2.20–3.00 (4H, m, aromatic H), and 7.63 (3H, s, SCH$_3$).

Anal. Calcd for C$_9$H$_8$N$_2$O$_2$S: C,51.91; H,3.87; N,13.45; S,15.37.

Found: C,51.79; H,3.86. N,13.37. S,15.41.

B. Desulfurization of 3-methylthio-4-nitroindole with Raney nickel gives 4-aminoindole.

EXAMPLE 13 - PREPARATION OF 5-CHLOROINDOLE

A. 5-Chloro-3-methylthioindole

This compound was obtained from 4-dichloroaniline and methylthioacetaldehyde dimethyl acetal by Method B giving 2.00 g (0.0102 mol, 23%) of product identical to that in Example 11 A.

B. Desulfurization with Raney nickel as described above gives 5-chloroindole.

EXAMPLE 14 - PREPARATION OF 5-METHYLINDOLE

A. 5-Methyl-3-methylthioindole

This compound was obtained from N-chloro-4-methylaniline and methylthioacetaldehyde dimethyl acetal by Method B which gave 2.75 g (0.017 mol, 39%) this intermediate product, bp 125°–126° (0.20 mm), n$^{25}$D 1.6332; ir 3340 l cm$^{-1}$ (NH); pmr (CCl$_4$), 2.45 (1H, s, NH), 2.55 (1H, s, aromatic H), 3.06 (3H, m, aromatic H), 7.57 and 7.75 (3H, s, CH$_3$ and SCH$_3$).

Anal. Calcd C$_{10}$H$_{11}$NS: C,67.75; H,6.26; N,7.90. Found: C,67.52; H,6.29; N,7.90.

B. Desulfurization of 5-methyl-3-methylthioindole (1.0 g, 5.65 mmol) gave an 82% yield of 5-methylindole, mp 55°–56.5° (lit. 58.5).

EXAMPLE 15 - PREPARATION OF 3-METHYLTHIO-4-NITROINDOLE

A. 3-Methylthio-4-nitroindole

This compound was obtained from N-chloro-3-nitroaniline and methylthioacetaldehyde dimethyl acetal following Method B giving 0.75 g (3.6 mmol, 38%) of the 3-Methylthio-4-nitroindole.

B. Desulfurization with Raney nickel as described above gives 4-aminoindole.

EXAMPLE 16 - PREPARATION OF 2-METHYL-5-NITROINDOLE

A. 2-Methyl-3-methylthio-5-nitroindole

To a suitable reaction vessel there was added 6.07 g (0.044 mol) of 4-nitroaniline dissolved in 300 ml of methylene chloride. The solution was cooled with vigorous stirring to −65°, giving a suspension of the nitro compound. A solution of 5.75 g (0.055 mol) of t-butyl hypochlorite in 10 ml of methylene chloride was added to form the 4-nitro-N-chloroaniline and subsequently after 3 hr, 7.4 g (0.071 mol) of methylthio-2-propanone in 10 ml of methylene chloride was added, while stirring was continued for 10 hr. to form the azasulfonium chloride salt. The triethylamine, 4.4 g (0.044 mol), dissolved in 10 ml of methylene chloride was added and the solution was warmed to room temperature to form the 2-methyl-3-methylthio-5-nitroindole. A 50-ml portion of water was added and after separation, the organic layer was extracted thoroughly with a 2N aqueous hydrochloric acid. Drying over anhydrous magnesium sulfate and filtration of the organic solution was followed by evaporation, leaving a solid residue that was stirred for several hrs. with 30 ml of benzene. The remaining precipitate was collected by filtration giving 2.92 g (0.013 mol, 30%) of 2-methyl-3-methylthio -5-nitroindole, mp 197.5°–198.5° (recr. from 95% ethanol); ir (KBr) 3250 cm$^{-1}$(NH); pmr (acetone-d$_6$) 1.40 (1H, br, s, NH), 1.02 (1H, d, J=2.0Hz, 4-aryl H), 2.02 (1H, dd, J=8.0 and 2.0 Hz, 6-aryl H), 2.57 (1H, d J=9.0 Hz, 7-aryl H) and 7.42 and 7.73 (3H, s, SCH$_3$ and CH$_3$).

Anal. Calcd for C$_{10}$H$_{10}$N$_2$O$_2$S: C,53.84; H,4.58; N,12.55; S,14.48. Found: C,54.05; H,4.54; N,12.50; S,14.42.

De-methylthiolation with Raney nickel gives the 2-methyl-5-aminoindole.

EXAMPLE 17 - PREPARATION OF 5-CARBOETHOXY-2-METHYLINDOLE

A. Following general procedure A above 5-carboethoxy-2-methyl-3-methylthioindole was prepared from the N-chloro-derivative of benzocaine and methylthio-2-propanone, with the modification that the suspension of benzocaine in 150 ml of methylene chloride was stirred for 30 minutes at −65° with the tert-butyl hypochlorite solution before addition of the sulfide. After addition of the methylthio-2-propanone, 100 ml of methylene chloride was added to promote stirring. Stirring was continued for 6 hours to insure complete reaction before addition of the base. The oily residue, obtained after work-up of the reaction mixture, was purified by stirring with 50 ml of ethyl ether, giving, upon filtration, 6.37 g (0.026 mol, 58% yield) of 5-carboethoxy-2-methyl-3-methylthioindole, m.p. 126°–127° C. (recrystallized from absolute ethanol); ir (KBr) 3250 (NH) and 1650 cm$^{-1}$ (C=O); pmr (CDCl$_3$) 0.84 (1H, s, NH), 1.35 (1H, d, J=1.5 Hz, 4-aryl H), 2.16 (1H, dd, J=8.0 and 1.5 Hz, 5-aryl H), 2.89 (1H, d J=8.0 Hz, 7-aryl H), 5.61 (2H, q, J=7.0 Hz, OCH$_2$), 7.52 and 7.80 (3H, s, CH$_3$ and SCH$_3$) and 8.59 (3H, t, J=7.0 Hz, OCH$_2$CH$_3$).

Anal. Calcd for C$_{13}$H$_{15}$NO$_2$S: C,62.63; H,6.06; N,5.62; S,12.86. Found: C,62.54; H,6.19; N,5.63; S,12.79.

B. 5-Carboethoxy-2-methylindole was obtained by desulfurization of 5-carboethoxy-2-methyl-3-methylthioindole, (1.0 g, 4.02 mmol), by the de-methylthiolation with Raney nickel giving 0.68 g (3.35 mmol, 83%) of 5-carboethoxy-2-methylindole, mp 140°–141° C. (recr. from benzene); ir (KBr) 3250 (NH) and 1650 cm$^{-1}$ (C=O); pmr (CDCl$_3$) 1.66 (2H, br, s, NH and 4-aryl H), 2.13 (1H, dd J=8.0 and 1.5 Hz, 6-aryl H), 2.83 (1H, d, J=8.0 Hz, 7-aryl H), 3.68 (1H, s, 3-aryl H), 5.60 (2H, q, J=7.0 Hz, OCH$_2$), 7.56 (3H, s, CH$_3$) and 8.58 (3H, t, J=7.0 Hz, OCH$_2$CH$_3$).

Anal. Calcd for C$_{12}$H$_{13}$NO$_2$: C,70.92; H,6.45; N,6.89 Found: C,71.07; H,6.43; N,6.87.

EXAMPLE 18 - PREPARATION OF 5-CARBETHOXYINDOLE

A. Following the general procedure A, 5-carboethoxy-3-methylthioindole was prepared by converting benzocaine to N-chlorobenzocaine, and reacting the N-chlorobenzocaine with methylthioacetaldehyde to form the azasulfonium salt therefrom, followed by treating the azasulfonium salt reaction mixture with triethylamine to form the 5-carboethoxy-3-methylthioindole.

In the work-up of the reaction mixture 50 ml of water was added after warming to room temperature, the layers were separated and the organic solution was concentrated. The residue was redissolved in 100 ml of ethyl ether, extracted with 2N aqueous hydrochloric acid to remove unreacted benzocaine, treated with sodium bicarbonate solution, dried over anhydrous magnesium sulfate, filtered and evaporated, leaving a residue that was subjected to column chromatography (silica gel). There was obtained 2.58 g (0.011 mol, 25%) of 5-carboethoxy-3-methylthioindole mp, 89.0°–90.5° (recr. from CCl$_4$); ir (KBr) 3220 (NH) and 1650 cm$^{-1}$ (C=O); pmr (CCl$_4$) 0.69 (1H, s, NH), 1.52 (1H, d, J=1.5 Hz, 4-aryl H), 2.10 (1H, dd J=8.0 and 1.5 Hz, 6-aryl H), 2.70 (2H, m, 2- and 7-aryl H), 5.56 (2H, q, J=7.0 Hz, OCH$_2$), 7.67 (3H, s, SCH$_3$), 8.54 (3H, t J=7.0 Hz, OCH$_2$CH$_3$).

Anal. Calcd for C$_{12}$H$_{13}$NO$_2$S: N,5.95; S,13.63. Found: N,5.74; S,13.32.

5-Carboethoxyindole was obtained by desulfurization of 5-carboethoxy-3-methylthioindole, (0.53 g, 2.25 mmol) in the manner described above giving 0.31 g (1.64 mmol, 73%) of 5-carboethoxyindole mp 94°–95° (recr. from cyclohexane); ir (KBr) 3320 (NH) and 1660 cm$^{-1}$(C=O); pmr (CCl$_4$) 0.68 (1H, s, NH), 1.60 (1H, br, s, 4-aryl H), 2.14 (1H, dd J=8.0 and 1.5 Hz, 6-aryl H), 2.70 (2H, m, aryl H), 3.48 (1H, m, aryl H), 5.62 (2H, q J=7.0 Hz, OCH$_2$) and 8.61 (3H, t, J=7.0 Hz, OCH$_2$CH$_3$).

Anal. Calcd for C$_{11}$H$_{11}$NO$_2$: C,69.83; H,5.86; N,7.40. Found: C,69.68; H,5.81; N,7.34.

EXAMPLE 19 - PREPARATION OF A MIXTURE OF 2,4-DIMETHYL-AND 2,6-DIMETHYL-INDOLES

A. Following the general procedure of A, m-toluidine was converted to the N-chloro-m-toluidine. The N-chloro-m-toluidine was reacted with methylthio-2-propanone to form the azasulfonium chloride salt. The azasulfonium chloride salt was reacted with triethylamine to form the mixture of the 2,4-dimethyl- and 2,6-dimethyl-3-methylthioindoles. After column chromatography (silica gel-methylene chloride) there was isolated 4.87 g (0.026 mol, 58%) of the substantially pure isomeric mixture (resp. ratio 41:59) as an oil: ir 3400 cm$^{-1}$(NH); pmr (CCl$_4$) 2.50–3.60 (4H, m, aryl H), 7.20 (s, 4, —CH$_3$), 7.65 (s, 6, —CH$_3$), 7.08, 7.93 and 7.96 (s, SCH$_3$ and 2-CH$_3$), all these singlets together account for an intergration of 9H.

B. Desulfurization of this mixture (2.52 g, 13.2 mmol) was accomplished by Raney nickel reduction procedures giving 1.19 g (8.25 mmol, 62.5%) of a mixture of 2,4-dimethyl- and 2,6-dimethylindole as a solid in a respective ratio of 34:66 pmr (CCl$_4$) 2.60–4.20 (5H, m, aryl H), 7.17, 7.62, 7.94 and 8.00 (s, CH$_3$ and SCH$_3$; total intergration for 6H).

Both mixtures could not be preparatively separated by available laboratory techniques.

EXAMPLE 20 - PREPARATION OF 3-METHYLTHIO-7-AZAINDOLE AND 7-AZAINDOLE

To a stirred solution of 2-aminopyridine (4.70 g, 0.05 mole) in 100 ml of methylene chloride at −65° was added dropwise a solution of a t-butyl hypochlorite (5.43 g, 0.05 mole) in 20 ml of methylene chloride cooled in a Dry-Ice/acetone bath to form the N-chloro-2-aminopyridine. The reaction mixture was stirred for 1 hr. Thiomethylacetaldehyde dimethyl acetal[1] (6.80 g, 0.05 mole) in 10 ml of methylene chloride cooled in a Dry-Ice acetone bath was introduced and stirred for 1.5 hr to form the azasulfonium salt. Sodium methoxide (3.0 g, 0.055 mole) in 50 ml of absolute methanol cooled in a Dry-Ice/acetone bath was added and the reaction mixture was stirred for 2.5 hr. Work-up of the reaction mixture by the standard procedure gave an intermediate which was mixed with potassium t-butoxide (5.6 g, 0.05 mole) in 300 ml of t-butyl alcohol. The mixture was refluxed for 5.5 hr. Rearrangement to the desired sulfide was shown to be complete by thin layer chromatography. Water was added to the reaction mixture when it was cooled to room temperature and the reaction mixture was extracted with diethyl ether. The combined ethereal extracts were concentrated on the rotary evaporator to give an oil which was taken up in 100 ml of 0.1 N aqueous hydrochloric acid and 100 ml of diethyl ether and stirred for 4.5 hr at room temperature. The aqueous layer was separated, basified with a saturated aqueous solution of sodium bicarbonate, and extracted with diethyl ether. The ethereal extracts were combined, dried, and concentrated to give crude 3-methylthio-7-azaindole (6.0 g) which was chromatographed on silica gel (Skelly Solve B and ethyl ether) to give white crystalline titled product (3.70 g, 45%), m.p. 115.0°–115.5°; nmr (CDCl$_3$) 2.36 (s, 3H), 7.35 (d of d, 1H), 7.50 (s, 1H), 8.10 (d of d, 1H), 8.40 (d of d, 1H), and 12.72 (broad s, 1H).

Exact Mass Molecular Weight. Calcd for $C_8H_8N_2S$: 164.0408. Found: 164.0410

Anal. Calcd for $C_8H_8N_2S$: C,58.51; H,4.91; N,17.06; S,19.52. Found: C,58.47; H,5.20; N,17.12; S,19.51. Demethylthiolation with Raney nickel gives 7-azaindole.

Footnote to Example 20: 1. E. H. Wick, T. Yaminishi, H. C. Wertheimer, Y. E. Hoff, B. E. Proctor, and S. A. Goldblith, *J. Agri. Food Chem.*, 9, 289 (1961).

EXAMPLE 21 - PREPARATION OF TETRAHYDROCARBAZOLE

A. 11-Methylthio-1,2,3,4-tetrahydrocarbazolenine was obtained by adding dropwise to a vigorously stirred solution of 0.044 mol of aniline in 150 ml of methylene chloride cooled to −65° a solution of 0.044 mol of t-butylhypochlorite in 20 ml of the same solvent. After a 5 min. period 0.044 mol of 2-methylthiocyclohexanone in 20 ml of methylene chloride was added causing a slight exotherm and stirring was continued for 1 hr. The intermediate azasulfonium salt did not precipitate. Subsequently, 0.044 mol of triethylamine in 20 ml of methylene chloride was added and after the addition was completed the cooling bath was removed to allow the solution to warm to room temperature. A 50-ml portion of water was added and the organic layer was separated, dried over anhydrous magnesium sulfate, filtered and evaporated. The residue was subjected to column chromatography (SiO$_2$-methylene chloride), giving 5.58 g (0.0257 mol, 58%) of 11-methylthio-1,2,3,4-tetrahydrocarbazolenine as an oil that solidified on standing in the refrigerator: mp 48°–50° (recr. from n-hexane), bp. 87°–88° (0.05 mm); ir 1690 cm$^{-1}$ (N=C); pmr (CCl$_4$)τ2.50–3.20 (4H, m, aryl-H), 7.00–8.95 (8H, m, aliphatic H), 8.84 (3H, s, SCH$_3$).

Anal. Calcd for $C_{13}H_{15}NS$: N,6.45. Found: N,6.40

(B). 1. Conversion of
11-Methylthio-1,2,3,4-tetrahydrocarbazolenine to
1,2,3,4-tetrahydrocarbazole This conversion was achieved by adding to an ice-cooled solution of 634 mg (2.92 mmol) of the thio-ether indolenine in 20 ml of anhydrous ether, portion wise 159 mg (4.18 mmol) of lithium aluminum hydride. The mixture was stirred for 40 min. at room temperature and then hydrolyzed with 30 ml of 0.5 N aqueous sulfuric acid. The layers were separated and the aqueous phase was extracted twice with 30-ml portions of ether. The combined organic solutions were treated with saturated sodium bicarbonate solution, dried over anhydrous magnesium sulfate, filtered and evaporated, leaving 520 mg (mp. 110°–116.5°) of a residue that was purified further by column chromatography (SiO$_2$-methylene chloride). In this way 400 mg (2.34 mmol, 80%) of 1,2,3,4-tetrahydrocarbazole, mp 114.5°–117° (lit. mp. 116°), was obtained.

(B) 2. Conversion of
11-Methylthio-1,2,3,4-tetrahydrocarbazolenine to
1,2,3,4-tetrahydrocarbazole This was achieved by refluxing a mixture of 687 mg (3.17 mmol) of the thio-ether indolenine and 363 mg (9.81 mmol) of sodium borohydride in 20 ml of isopropanol for 16 hr. A 20-ml portion of water was added and the mixture was extracted twice with 30-ml portions of methylene chloride. The organic extracts were dried over anhydrous magnesium sulfate, filtered, and evaporated, leaving 500 mg (mp 105°–111°) of a residue, that was purified further over a column (SiO$_2$-methylene chloride). In this manner 438 mg (2.02 mmol, 64%) of 1,2,3,4-tetrahydrocarbazole, mp. 111°–114° was obtained.

(B) 3. Conversion of
11-Methylthio-1,2,3,4-tetrahydrocarbazolenine to
1,2,3,4-tetrahydrocarbazole This was achieved by stirring 798 mg (3.67 mmol) of the thio-ether indolenine in 30 ml of absolute ethanol for 30 min with 2 spoons of Ra-Ni W-2. Workup as for the formerly described desulfurizations gave 521 mg (3.05 mmol, 83%) of 1,2,3,4-tetrahydrocarbazole, mp. 115°–117.5°.

Additional compounds which can be prepared by the procedures described above include:
5-cyanoindole from N-chloro-4-cyanoaniline and methylthioacetaldehyde;
6-(N,N-diethylamino)indole from N-chloro-3-(N,N-diethylamino) aniline and methylthioacetaldehyde;
4,5-dichlorindole from N,3,4-trichloroaniline and methyltrioacetaldehyde;
6-propionoxy-2-methylindole from N-chloro-3-propionoxyaniline and methylthioacetone;
5-butoxycarbonylindole from N-chloro-4-butoxycarbonylaniline and methylthioacetaldehyde;
6-phenoxycarbonylindole from N-chloro-3-phenoxycarbonylaniline and methylthioacetaldehyde;
N,5-dimethylindole from N-chloro-N-methyl-4-methylaniline and methylthioacetaldehyde;
N-benzyl-5-nitroindole from N-chloro-N-benzyl-4-nitroaniline and methylthioacetaldehyde;
N-phenyl-5-cyanoindole from N-chloro-N-phenyl-4-cyanoaniline and methylthioacetaldehyde;
N-propyl-2-methylindole from N-chloro-N-propylaniline and methylthioacetone;
5-azaindole from 4-(N-chloroamino) pyridine and methylthioacetaldehyde;
4-aza-7-chloroindole from 3-(N-chloroamino)-6-chloropyridine and methylthioacetaldehyde;
5-chloro-3-methylindole from N,4-dichloroaniline and 2-(methylthio)-propionaldehyde;
2,3-dimethylindole from N-chloroaniline and 3-methylthio-2-butanone;
6-methyltetrahydrocarbazole from N-chloro-p-toluidine and 3-methylthio-2-butanone;

6-aza-2-benzylindole from 4-(N-chloroamino) pyridine and 1-methylthio-3-phenyl acetone, and the like.

The acetal or ketal forms of the β-carbonyl sulfide reactants can be used to prepare the compounds by the Method B procedure.

I claim:

1. A compound of the formula:

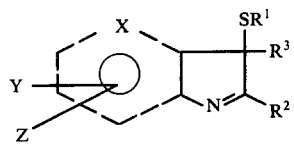

wherein

X is —C≡;

each of Y and Z is fluorine, chlorine, bromine iodine, nitro, cyano, N,N-di-lower alkylamino, lower alkyl, lower alkyloxy, lower-alkanoyloxy, a carbonyloxy-lower alkyl or a carbonyloxy-phenyl group;

$R^1$ is lower-alkyl or phenyl;

and $R^2$ and $R^3$, taken together with the carbons to which they are bonded, complete a ring of 5 to 8 carbon atoms.

2. A compound according to claim 1, wherein $R^2$ and $R^3$ are taken together with the carbons to which they are bonded to complete a ring of 6 carbon atoms.

3. A compound of claim 2 which is 11-methylthio-1,2,3,4-tetrahydrocarbazolenine.

* * * * *

UNITED STATES PATENT AND TRADEMARK OFFICE
CERTIFICATE OF CORRECTION

PATENT NO. : 4,080,341

DATED : March 21, 1978

INVENTOR(S) : Gassman, Paul G.

It is certified that error appears in the above-identified patent and that said Letters Patent are hereby corrected as shown below:

Col. 3, line 66; "pka" should read --pKa--

Signed and Sealed this

Nineteenth Day of September 1978

[SEAL]

Attest:

RUTH C. MASON
Attesting Officer

DONALD W. BANNER
Commissioner of Patents and Trademarks